United States Patent [19]

Aoyagi

[11] 4,271,306
[45] Jun. 2, 1981

[54] 2-ARYLTHIO-4,4-DIALKYL-5-METHYLENE-1,3-THIAZOLINES

[75] Inventor: Edward I. Aoyagi, Petaluma, Calif.

[73] Assignee: Chevron Research Company, San Francisco, Calif.

[21] Appl. No.: 115,654

[22] Filed: Jan. 28, 1980

[51] Int. Cl.³ .......................................... C07D 277/08
[52] U.S. Cl. .................................. 548/182; 424/276
[58] Field of Search ............. 548/190, 195, 147, 182; 424/270

[56] References Cited

U.S. PATENT DOCUMENTS 3,201,409   8/1965   Spivak et al. .................. 548/195

Primary Examiner—Nicholas S. Rizzo

Attorney, Agent, or Firm—D. A. Newell; T. G. DeJonghe; R. J. Suyat

[57] ABSTRACT

Compounds of the formula

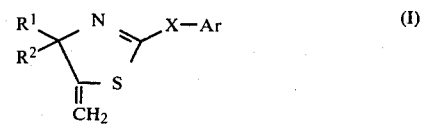

wherein $R^1$ and $R^2$ are alkyl or $-(CH_2)_n-$ wherein n=4 through 7; X is sulfur or $NR^3$ wherein $R^3$ is alkyl, alkenyl, alkynyl or cycloalkyl; Ar is an aromatic group of 6 to 12 carbon atoms substituted with 1 to 5 halo groups, 2 nitro groups, or 1 to 5 haloalkyl groups have bactericidal and fungicidal activity.

4 Claims, No Drawings

2-ARYLTHIO-4,4-DIALKYL-5-METHYLENE-1,3-THIAZOLINES

BACKGROUND OF THE INVENTION

Azerbaev et al disclose 2-benzylamino-4,4-dialkyl-5-methylene-1,3-thiazolines in *Chem. Abstr.* 79:66237 v (1973).

Eloy et al disclose 2-alkylamino-5-methylene-thiazoles in *Chem. Abstr.* 81:13439x(1974).

SUMMARY OF THE INVENTION

The present invention relates to novel bactericidal compounds, compositions thereof and methods of their use. I have found that bactericidal activity is particularly responsive to the nature of the 2-position and 4-position substituents on 4,4-dialkyl-5-methylene-1,3-thiazolines.

In general, it has been found that 2-arylamino and 2-arylthio groups produce bactericidal activity whereas 2-alkylamino or 2-alkylthio groups do not.

DESCRIPTION OF THE INVENTION

The present invention relates to compounds of the formula I:

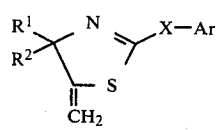

wherein $R^1$ and $R^2$ are independently alkyl of 1 to 4 carbon atoms or $R^1$ and $R^2$ are joined to form a cycloalkyl group of 5 to 8 carbon atoms;

X is sulfur or

wherein $R^3$ is alkyl of 1 to 6 carbon atoms, alkenyl or alkynyl of 2 to 4 carbon atoms or cycloalkyl of 5 or 6 carbon atoms;

Ar is an aromatic group of 6 to 12 carbon atoms, optionally substituted with 1 to 5 halo groups, two nitro groups, or 1 to 5 haloalkyl groups containing 1 to 3 carbon atoms and 1 to 7 halogen atoms.

Representative $R^1$ and $R^2$ groups are methyl, ethyl, l-propyl, n-propyl, n-butyl, or $R^1$, and $R^2$ are joined to form —CH₂CH₂CH₂CH₂— or —CH₂CH₂CH₂CH₂CH₂—.

Representative $R^3$ groups are methyl, ethyl, propyl, butyl, pentyl, hexyl, vinyl, allyl, butenyl, acetylenyl, propargyl, cyclopentyl and cyclohexyl.

Representative Ar groups are 2,6-dinitro-4-trifluoromethylphenyl, 2,4-dichlorophenyl, 4-chlorophenyl, 4-trifluoromethylphenyl, 1-methylnaphth-2-yl and p-biphenyl.

Preferably $R^1$ and $R^2$ are methyl, X is sulfur and Ar is 2,6-dinitro-4-trifluoromethylphenyl. When X is $NR^3$, $R^3$ is preferably allyl.

The compounds of the invention may be made according to the following scheme:

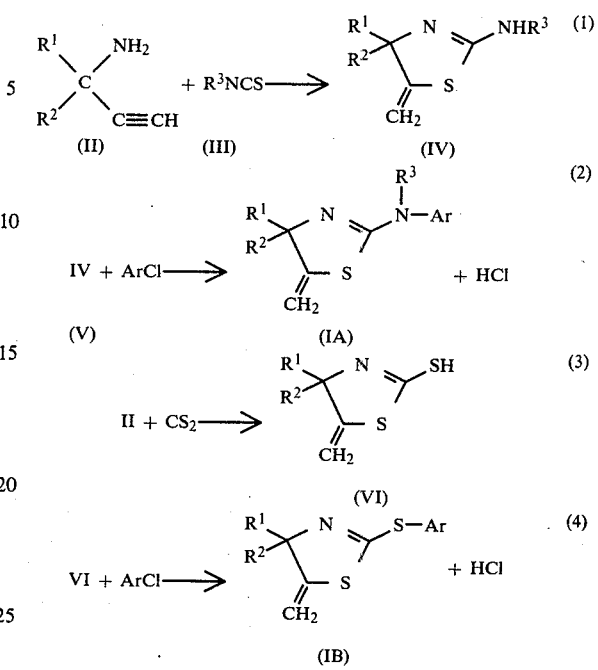

Reactions (1) and (3) are conventional condensations and may be performed by reacting substantially equimolar portions of the amino propargyl compound (II) with either the thiocyano compound (III) or carbon disulfide to form, respectively, the cyclic intermediates (IV) and (VI). The reaction may be conducted in a suitable inert solvent at 10° C. to 100° C., preferably at about 20° C.–30° C.

Reactions (2) and (4) are conventional substitution reactions which may be performed by reacting substantially equimolar amounts of the cyclic compound (IV or VI) with the chloroaryl compound in an inert diluent, preferably in presence of an organic base, such as, triethylamine, to serve as a scavenger for the evolved hydrogen chloride. The reaction may be carried out at room temperature.

Compounds (IA) may also be expeditiously prepared according to reactions (1a) and (1b):

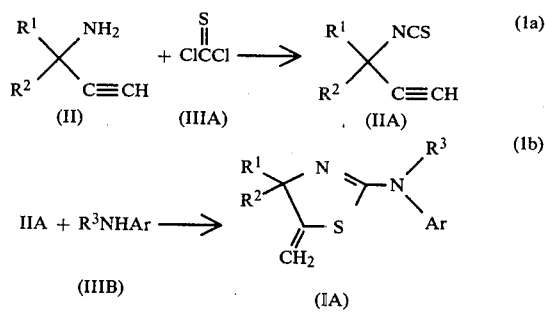

Reaction (1a) may be conducted in an inert organic diluent, preferably with water as a co-solvent. An organic base, such as a trialkylamine, may be added to scavenge the evolved hydrogen chloride. The reaction is exothermic and the mixture may be cooled to prevent boiling the solvent. The reaction is preferably carried out at room temperature employing a slight molar excess of thiophosgene (IIIA).

Reaction (1b) may be conducted with substantially equimolar amounts of (IIA) and amine (IIIB) in an inert organic diluent. The exothermic reaction may be conducted at 0°–100° C., preferably at 20°–40° C.

The compounds of this invention are useful for controlling pathogens such as bacteria and fungi. The compounds of the invention are particularly effective in the control of bacteria. When used as bactericides, the compounds of this invention are formulated and applied in bactericidal amounts by conventional art methods to bacteria or hosts (growth environment) which are subject to bacterial attack, especially vegetative hosts such as plants, plant seeds, etc. The amount used will, of course, depend on several factors such as the host, the type of bacteria, and the particular active compound used.

The compounds of this invention may be combined with inert liquids and solid carriers such as powders, solutions, dispersions, etc., for such use. Generally, they will be admixed with biologically inert liquids or solids in an amount from about 0.05 to 95 weight percent. Higher or lower amounts, of course, can be used. Preferably from 1 to 50 weight percent of the composition will be the active compound of this invention.

Typical solid carriers which are essentially used to formulate the bactericides are clay, talc, chalk and sawdust. Representative solvents which are suitably used include aromatic hydrocarbons such as xylene, benzene, toluene, petroleum fractions, alcohols (especially low molecular weight alkanols) and chlorinated aliphatic hydrocarbons such as chloroform, methylene chloride and the like. These formulations may also contain emulsifying agents, sticking agents, fillers and other compatible pesticides.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLE 1

Bactericidal Efficacy

This method is designed to test candidate toxicants in vitro against *Pseudomonas syringae, Erwinea amylovora* and *Xanthomonas vesicatoria*. The bacteria are cultured on Emerson Agar slants collected and placed in aqueous suspensions which exhibit 50% light transmittance (vs. sterile deionized water) at 610 millimicrons. These suspensions are diluted in sterile deionized water in 1:19 ratio and used to inoculate test plates. Petri dishes containing 20 ml Difco Dehydrated Emerson Agar are sprayed with 50 mg of the diluted inoculum.

The inoculated cultures are then sprayed with 70 microliters of a 500-ppm acetone or water solution of the test compound.

Each treatment is conducted on duplicate plates and incubated at 23.5° C. for 24 hours.

The zone of inhibited growth is measured as a diameter of a circle wherein the bacteria has not multiplied. The inhibition diameters are compared to a calibration chart which correlates diameter to $ED_{99}$ dosage. The percentage of the $ED_{99}$ of the test sample of the $ED_{99}$ of the control standard, phenyl mercuric acetate, is given in Table II.

EXAMPLE 2

Mycelial Inhibition

A number of the compounds of the present invention were evaluated for fungicidal effectiveness by means of a mycelial inhibition test. This test is designed to measure the fungitoxic activity of fungicidal chemicals in terms of their degree of inhibition of mycelium growth. Each compound to be tested was dissolved in acetone to 500 ppm concentration. Paper strips were inoculated with the particular mycelium growth by covering the paper with a potato dextrose broth culture of mycelial suspension. The inoculated papers were then placed on potato dextrose agar plates and sprayed by means of a micro sprayer with the fungicidal solution. The treated paper strips were incubated at 25° C. and data is taken after 24 hours. Fungicidal activities are measured by a zone of inhibited mycelial growth from the center of the paper strip in terms of $Mg/cm^2$ needed for 99% control of the fungus ($ED_{99}$). The effectiveness of the compounds tested for fungicidal activity is reported in Table III in terms of the percent of the $ED_{99}$ of the test compound of the $ED_{99}$ of the standard Difolatan ®.

EXAMPLE 3

Preparation of 2-(2,6-dinitro-4-trifluoromethylphenylthio)-4,4-dimethyl-5-methylene-1,3-thiazoline A. To 3-amino-3-methyl-butyne (134 g, 90% purity) in carbon tetrachloride (250 ml) was added carbon disulfide (120 ml) with stirring at ice bath temperature. Stirring was continued for 3 days at room temperature under a cold water condensor.

Methylene chloride was added and the water (an impurity in the butyne) was separated. The organic phase was dried ($MgSO_4$) and stripped to yield 171 g of 2-mercapto-4,4-dimethyl-5-methylene-1,3-thiazoline (A).

B. To A (10 g) and triethylamine (7 g) in benzene (100 ml) was added 2,6-dinitro-4-trifluoromethyl-1-chlorobenzene (17.4 g). The mixture was refluxed overnight and filtered. The filtrate was washed ($H_2O$), dried ($MgSO_4$), filtered and stripped. The solid was crystallized in hexane to yield the title product, 14 g, mp 76°-79° C.

EXAMPLE 4

Preparation of 3-(2,6-dinitro-4-trifluoromethylphenylthio)-1-methylene-2,4-thiazaspiro[5.4]decane A. 1-Ethynyl-1-amino-cyclohexane (12.3 g) and carbon disulfide (8.2 g) were treated as in Example 3A to yield 12 g 3-mercapto-1-methylene-2,4-thiazaspiro[5.4]decane (B, m.p. 162°–3° C.).

B. 2,6-Dinitro-4-trifluoromethyl-1-chlorobenzene, (18.1 g) triethylamine (5.7 g) and B (10 g) were treated as in Example 3B to yield 16 g of the title product, m.p. 81°–85° C.

EXAMPLE 5

Preparation of 3-(N-2,6-dinitrophenyl-N-methyl)amino-1-methylene-2,4-thiazaspiro[5.4]decane A. 1-Ethynyl-1-amino-cyclohexane (123 g) and methylisothiocyanate (73 g) were treated as in Example 3A.

The product was dissolved in 500 ml chloroform and refluxed gently for 3 hours, stripped and the product was recrystallized in chloroform-hexane to yield 107 g 3-methylamino-1-methylene-2,4-thiazaspiro[5.4]decane (C).

B. 2,6-Dinitro-4-trifluoromethyl-1-chlorobenzene (7.6 g), triethylamine (2.87 g) and C (5.5 g) was treated as in Example 3B.

The product was filtered through a silica column (100 g) and recrystallized from hexane to yield 2.6 g of the title product m.p. 81°–85° C.

EXAMPLE 6

Preparation of 2-(N-2,6-dinitro-4-trifluoromethylphenyl-N-allyl)amino-4,4-dimethyl-5-methylene-1,3-thiazoline A. 3-Amino-3-methyl-butyne (91.3 g) and allylthiocyanate (54.3 g) were treated as in Example 3A to yield 2-allylamino-4,4-dimethyl-5-methylene-1,3-thiazoline (D, m.p. 82°–85° C.).

B. 2,6-Dinitro-4-trifluoromethyl-1-chlorobenzene (14.8 g), triethylamine (6 g) and D (10 g) were treated as in Example 5B to yield 10 g of the title product.

TABLE 1

COMPOUNDS OF THE FORMULA

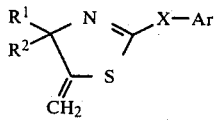

(I)

| No. | X | $R^1$ | $R^2$ | Ar | m.p., °C. | Analysis S Calculated | Found |
|---|---|---|---|---|---|---|---|
| 1 | S | $-(CH_2)_5-$ | | (1) | 81–85 | 14.80 | 15.2 |
| 2 | S | $CH_3$ | $CH_3$ | (1) | 76–79 | 16.31 | 16.4 |
| 3 | $NCH_3$ | $-(CH_2)_5-$ | | (1) | 81–85 | 7.45 | 7.7 |
| 4 | $NCH_2CH=CH_2$ | $-(CH_2)_5-$ | | (1) | oil | 7.03 | 7.2 |
| 5 | $NCH_2CH=CH_2$ | $CH_3$ | $CH_3$ | (1) | oil | 7.70 | 7.0 |
| 3A | NH | $-(CH_2)_5-$ | | $CH_2\phi$ | 56–58 | 11.77 | 10.9 |
| 3B | NH | $-(CH_2)_5-$ | | $CH_2-\text{(3-pyridyl)}$ | 98–100 | 11.73 | 12.3 |
| 3C | NH | $-(CH_2)_5-$ | | $-(CH_2)_3\phi$ | oil | 10.20 | 11.1 |
| 3D | NH | $-(CH_2)_5-$ | | (2) | 82–84 | 10.13 | 10.6 |
| 3E | NH | $-(CH_2)_5-$ | | $CH_2-\text{(4-Cl-phenyl)}$ | oil | 10.45 | 10.7 |
| 3F | NH | $-(CH_2)_5-$ | | $CH_2CH_2\phi$ | oil | 11.20 | 11.5 |
| 6A | $NCH_3$ | $-(CH_2)_5-$ | | $PO(OC_2H_5)_2$ | oil | 9.65 | 10.6 |
| 6B | $NC_2H_5$ | $-(CH_2)_5-$ | | $PO(OC_2H_5)_2$ | oil | 9.26 | 9.8 |

(1) = 2,6-dinitro-4-trifluoromethylphenyl (2) = 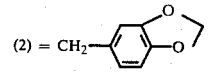

TABLE II

| | Bactericidal Efficacy Percent Control (Example 1) | | |
|---|---|---|---|
| No. | Pseud. | Erwinia | Xanth. |
| 1 | 35 | 0 | 0 |
| 2 | 69 | 97 | 0 |
| 3 | 36 | 41 | 97 |
| 4 | 0 | 43 | 97 |
| 5 | 100 | 65 | 0 |
| 3A | 0 | 0 | 0 |
| 3B | — | — | 0 |
| 3C | 0 | 0 | 0 |
| 3D | 0 | 0 | 0 |
| 3E | — | — | 0 |
| 3F | 0 | 0 | 0 |
| 6A | 0 | 0 | 0 |
| 6B | 0 | 0 | 0 |

TABLE III

| | Mycelial Inhibition Percent of Standard (Example 2) | | | | |
|---|---|---|---|---|---|
| No. | P | R | F | B | A |
| 1 | 0 | — | 0 | 0 | 0 |
| 2 | 61 | — | 0 | 0 | 129 |
| 3 | 0 | — | 0 | 0 | 0 |
| 4 | 0 | — | 0 | 0 | 0 |
| 5 | 0 | 0 | 0 | 0 | 0 |

TABLE III-continued

Mycelial Inhibition
Percent of Standard (Example 2)

| No. | P | R | F | B | A |
| --- | --- | --- | --- | --- | --- |
| 3A | 0 | 0 | 0 | 0 | 0 |
| 3B | 0 | 0 | 0 | 0 | 0 |
| 3C | 0 | 0 | 0 | 0 | 0 |
| 3D | 0 | 0 | 0 | 0 | 0 |
| 3E | 0 | 0 | 0 | 0 | 0 |
| 3F | 0 | 0 | 0 | 0 | 0 |

P = *Pythium ultimum*
R = *Rhizoctonia solani*
F = *Fusarium moniloforma*
B = *Botrytis cinerea*
A = *Aspergillus niger*

What is claimed is:

1. A compound of the formula

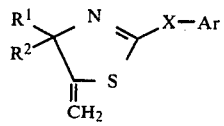

wherein
  $R^1$ and $R^2$ are independently alkyl of 1 to 4 carbon atoms or $R^1$ and $R^2$ are joined to form cycloalkyl of 5 to 8 carbon atoms;
  X is sulfur;
  Ar is phenyl, naphthyl or biphenyl, optionally substituted with 1 to 5 halo groups, two nitro groups, or 1 to 5 haloalkyl groups of 1 to 3 carbon atoms and 1 to 7 halogen atoms.

2. A compound according to claim 1 wherein X is sulfur.

3. A compound according to claim 2 wherein $R^1$ and $R^2$ are alkyl of 1 to 4 carbon atoms.

4. The compound according to claim 3 wherein $R^1$ and $R^2$ are methyl and Ar is 2,6-dinitro-4-trifluoromethylphenyl.

* * * * *